United States Patent
Orr

(10) Patent No.: US 9,572,518 B2
(45) Date of Patent: Feb. 21, 2017

(54) SYSTEM AND METHOD FOR DETECTING VALID BREATHS FROM A CAPNOMETRY SIGNAL

(75) Inventor: Joseph Allen Orr, Park City, UT (US)

(73) Assignee: Koninklijke Philips N.V., Eindhoven (NL)

( * ) Notice: Subject to any disclaimer, the term of this patent is extended or adjusted under 35 U.S.C. 154(b) by 975 days.

(21) Appl. No.: 13/518,985

(22) PCT Filed: Dec. 28, 2010

(86) PCT No.: PCT/IB2010/056096
§ 371 (c)(1),
(2), (4) Date: Jun. 25, 2012

(87) PCT Pub. No.: WO2011/080701
PCT Pub. Date: Jul. 7, 2011

(65) Prior Publication Data
US 2012/0265089 A1   Oct. 18, 2012

Related U.S. Application Data

(60) Provisional application No. 61/290,539, filed on Dec. 29, 2009.

(51) Int. Cl.
*A61B 5/08* (2006.01)
*A61B 5/083* (2006.01)
*A61B 5/00* (2006.01)
*G01N 33/00* (2006.01)

(52) U.S. Cl.
CPC .......... *A61B 5/0836* (2013.01); *A61B 5/7221* (2013.01); *A61B 5/0816* (2013.01); *G01N 33/0018* (2013.01)

(58) Field of Classification Search
CPC ... A61B 5/0816; A61B 5/0836; A61B 5/7221; G01N 33/0018
USPC ................................................... 600/529–543
See application file for complete search history.

(56) References Cited

U.S. PATENT DOCUMENTS

2002/0017300 A1   2/2002   Hickle
2011/0009763 A1*  1/2011   Levitsky et al. .............. 600/532

FOREIGN PATENT DOCUMENTS

| EP | 2204206 A1 | 7/2010 |
| JP | 61100231 A | 5/1986 |
| WO | 2009133561 A1 | 11/2009 |

* cited by examiner

*Primary Examiner* — Navin Natnithithadha
*Assistant Examiner* — Eric Messersmith

(57) ABSTRACT

Based on a capnometry signal, one or more breathing parameters of a subject are determined that require valid breaths by the subject to be distinguished from anatomical events that cause the $CO_2$ content of gas at or near the airway of the subject to fluctuate. To improve the accuracy of one or more of these determinations, gas at or near the airway of the subject is diluted.

21 Claims, 2 Drawing Sheets

SYSTEM AND METHOD FOR DETECTING VALID BREATHS FROM A CAPNOMETRY SIGNAL

BACKGROUND OF THE INVENTION

1. Field of the Invention

The invention relates to distinguishing between anatomical events that cause the carbon dioxide ($CO_2$) content of gas at or near the airway of a subject to fluctuate and valid breaths by the subject from a capnometry signal.

2. Description of the Related Art

Capnometry systems that generate output signals conveying information related to the $CO_2$ content of gas at or near the airway of a subject are known. Generally, these signals can be used to detect breathing by the subject. However, conventional systems can confuse anatomical events that cause the $CO_2$ content of gas at or near the airway of a subject to fluctuate with valid breathing by the subject.

SUMMARY OF THE INVENTION

One aspect of the invention relates to a system configured to monitor respiration of a subject. In one embodiment, the system comprises a subject interface appliance, a sampling chamber, a sensor, a processor, and a diluting flow generator. The subject interface appliance has a sampling interface including a gas inlet and a gas outlet, and is configured to be installed at or near the airway of the subject such that gas from the airway of the subject is drawn into the gas inlet. The gas outlet is arranged near the gas inlet. The sampling chamber is in fluid communication with the subject interface appliance such that gas drawn from the airway of the subject that is drawn into the gas inlet flows into the sampling chamber. The sensor is configured to generate an output signal conveying information related to the carbon dioxide content of gas in the sampling chamber. The processor is configured to determine, from the output signal generated by the sensor, one or more parameters of the respiration of the subject. The diluting flow generator is configured to generate a diluting flow of gas, and is in fluid communication with the subject interface appliance such that the diluting flow of gas is emitted from the gas outlet at or near the gas inlet. The diluting flow of gas is substantially free of carbon dioxide, and is emitted by the gas outlet with a flow rate and directionality (i) that dilutes gas from the airway of the subject prior to the gas being drawn into the gas inlet of the subject interface appliance such that the processor is able to distinguish between breaths and other anatomical events that cause fluctuations in carbon dioxide content in the airway of the subject, and (ii) that does not impact the respiration of the subject.

Another aspect of the invention relates to a method of monitoring respiration of a subject. In one embodiment, the method comprises drawing gas through a gas inlet positioned at or near the airway of a subject and into a sampling chamber; generating an output signal conveying information related to the carbon dioxide content of gas in the sampling chamber; determining, from the output signal generated, one or more parameters of the respiration of the subject; generating a diluting flow of gas that is substantially free of carbon dioxide; and emitting the diluting flow of gas at a location and flow rate (i) that dilutes gas from the airway of the subject prior to the gas being drawn into the gas inlet of the subject interface appliance such that the processor is able to distinguish between breaths and other anatomical events that cause fluctuations in carbon dioxide content in the airway of the subject, and (ii) that does not impact respiration of the subject.

Yet another aspect of the invention relates to a system configured to monitor respiration of a subject. In one embodiment, the system comprises means for drawing gas through a gas inlet positioned at or near the airway of a subject and into a sampling chamber; means for generating an output signal conveying information related to the carbon dioxide content of gas in the sampling chamber; means for determining, from the output signal generated, one or more parameters of the respiration of the subject; means for generating a diluting flow of gas that is substantially free of carbon dioxide; and means for emitting the diluting flow of gas at a location and flow rate (i) that dilutes gas from the airway of the subject prior to the gas being drawn into the gas inlet of the subject interface appliance such that the processor is able to distinguish between breaths and other anatomical events that cause fluctuations in carbon dioxide content in the airway of the subject, and (ii) that does not impact respiration of the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
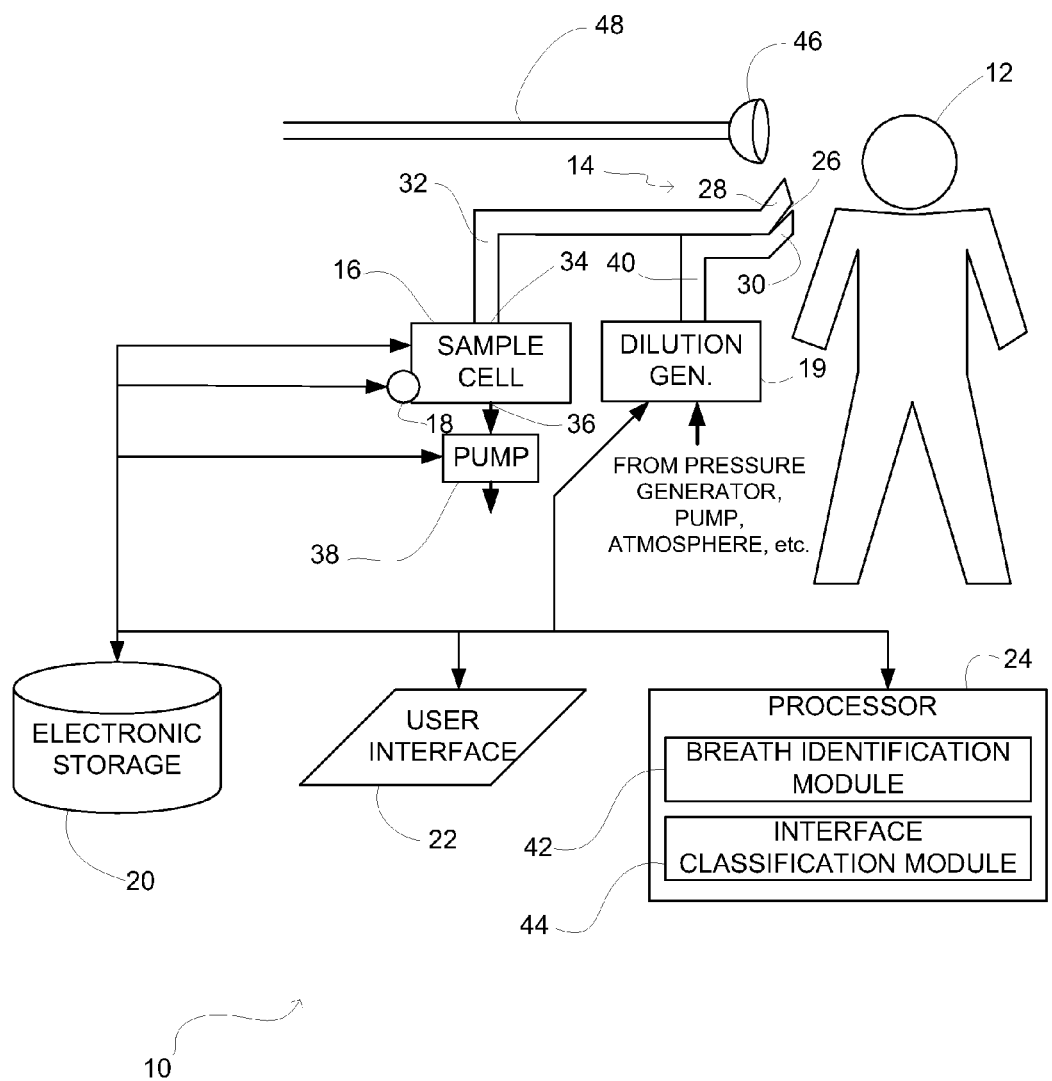
FIG. 1 illustrates a system configured to monitor the breathing of a subject, in accordance with one or more embodiments of the invention.

FIG. 1 illustrates a system 10 configured to monitor the breathing of a subject 12. In one embodiment, system 10 is configured to perform sidestream capnometry to determine information related to the composition of gas at or near the airway of subject 12. Based on such information system 10 determines one or more breathing parameters of subject 12 (e.g., respiratory rate, breathing transitions, valid breath identification, end-tidal $CO_2$, etc.) and/or performs other functions. To improve the accuracy of one or more of these determinations, system 10 may further dilute gas in the airway of the subject. This may enhance accuracy in determining breathing parameters that require distinguishing between valid breaths and anatomical events other than breaths causing fluctuations in $CO_2$ content in the airway of subject 12. In one embodiment, system 10 includes one or more of an interface appliance 14, a sample cell 16, a composition detector 18, diluting flow generator 19, electronic storage 20, a user interface 22, one or more processors 24, and/or other components.

The interface appliance 14 is configured to communicate with an airway of subject 12. To communicate with an airway of subject 12, interface appliance 14 engages one or more external orifices of the airway of subject 12. The interface appliance 28 may engage the one or more external orifices of the airway of subject 12 in a sealed or unsealed manner. The interface appliance 14 may include, for example, one or more of a nasal cannula, a nasal mask, a nasal/oral mask, a full face mask, a total face mask, a partial rebreathing mask, or other interface appliances configured to communicate with an airway of a subject. The present invention is not limited to these examples, and contemplates implementation of any subject interface.

The interface appliance 14 includes a sampling interface 26. The sampling interface 26 includes a gas inlet 28 and a gas outlet 30. The sampling interface 26 is configured such that if interface appliance 14 is installed on the face of subject 12, sampling interface 26 is engaged with one or more external orifices of the airway of subject 12 to draw gas from the airway of subject 12 through gas inlet 28. For example, in one embodiment, sampling interface 26 includes a nasal cannula forming gas inlet 28 to draw gas from one or both of the nares of subject 12. In this embodiment, the prong(s) of the cannula on which gas inlet 28 is formed are inserted into the nares of subject 12 such that gas inlet 28 is in fluid communication with the airway of subject 12.

Gas drawn into sampling interface 26 through gas inlet 28 is communicated to sample cell 16 via a sampling conduit 32. The sampling conduit 32 may be formed from a resilient material to form a flow path between gas inlet 28 and gas outlet 30.

The sample cell 16 is configured to hold gas in isolation from atmosphere, and includes an inlet 34 and an outlet 36. The sample cell 16 is in fluid communication with sampling conduit 32 to receive gas from sampling conduit 32 through inlet 34. Gas is exhausted from sample cell 16 through outlet 36. The gas may be exhausted, for example, to atmosphere, provided by to interface appliance 14 (e.g., as discussed below), and/or otherwise exhausted. In one embodiment, a pump 38 is placed in fluid communication with outlet 36 to draw gas from the airway of subject 12 into sampling interface 26 through gas inlet 28 and in and through sample cell 16.

By virtue of the fluid communication between sample cell 16 and the airway of subject 12 while interface appliance 14 is installed on subject 12, the sample cell 16 holds gas having one or more gas parameters that are the same as, similar to, or impacted by the gas parameters of gas at the airway of subject 12. For example, the composition of the gas within sample cell 16 is similar to or the same as the gas drawn from the airway of subject 12 into gas inlet 28.

The composition detector 18 is a sensor configured to generate output signals conveying information related to the $CO_2$ content of gas received into sample cell 16 from sampling conduit 32. The composition detector 18 may include one or more components in direct contact with the gas inside of sample cell 16 (e.g., located within sample cell 16) to detect the information related to the composition of gas in sample cell 16. By way of non-limiting example, the composition detector 18 may include a photoluminescent material disposed in sample cell 16 in direct contact with gas therein.

As is discussed further below, in one embodiment, the output signals generated by composition detector 18 are implemented to determine one or more parameters of the breathing of subject 12 that require discrimination between valid breaths by subject 12 and other anatomical events that cause the $CO_2$ content of gas at or near the airway of subject 12 to fluctuate. By way of non-limiting example, cardiogenic oscillations involving the beating of the heart against the side of the lungs may cause small, ineffective movements of gas in and out of the airway of subject 12 that cause the $CO_2$ content of gas at or near the airway of subject 12 to fluctuate. As another non-limiting example, attempted breathing through an obstructed, or partially obstructed airway, may result in small, ineffective movements of gas in and out of the airway of subject 12 caused by movement of the glottis as subject 12 attempts to breath. These small movements of gas may also cause fluctuations in the content of $CO_2$ in the gas at or near the airway of subject 12.

In conventional systems, since composition detector 18 does not provide reliable information about volume or flow rate of gas within the airway of subject 12, gas samples taken from the airway of subject 12 during an anatomical event that causes the $CO_2$ content of gas at or near the airway of subject 12 to fluctuate may not be discriminated from valid breaths based solely on the output signals of composition detector 18. However, in system 10, measures are taken to permit distinction between such events and valid breaths based on the output signals of composition detector 18.

In system 10, diluting flow generator 19 is configured to generate a diluting flow of gas. The diluting flow of gas contains no, or substantially no (e.g., less than 0.1%) $CO_2$, or a known level of $CO_2$. In one embodiment, diluting flow generator 19 includes a source of gas (e.g., wall gas, a Dewar, a canister, etc.) that has no, or substantially no $CO_2$. In one embodiment, diluting flow generator 19 includes components capable of removing $CO_2$ from gas. For example, diluting flow generator 19 may be configured to receive gas exhausted from sample cell 16 (e.g., through pump 38), and remove $CO_2$ from the received gas. The diluting flow generator 19 may be configured to selectively control the pressure and/or the flow rate of the diluting flow of gas. To control one or both of these parameters, diluting flow generator 19 may include one or more of a blower, a bellows, a turbine, a controllable valve, and/or other components.

The diluting flow of gas generated by diluting flow generator 19 is communicated to gas outlet 30 of sampling interface 26 via a dilution conduit 40. The dilution conduit 40 may be formed from a resilient, flexible material that provides a sealed (or substantially sealed) flow path between diluting flow generator 19 and gas outlet 30. In one embodiment, dilution conduit 40 is formed as a dual lumen system with sampling conduit 32. In one embodiment, dilution conduit 40 and sampling conduit 32 are formed separately.

The gas outlet 30 of sampling interface 26 is configured to release the diluting flow of gas into the body of gas from which gas is drawn into gas inlet 28. As such, in one embodiment, gas outlet 30 is formed on sampling interface 26 adjacent to gas outlet 30. The release of the diluting flow of gas into the body of gas from which gas is drawn by gas inlet 28 dilutes the gas from the airway of subject 12 that is received into gas inlet 28 and pump 38 for measurement by composition detector 18. This dilution enables discrimination between anatomical events that cause the $CO_2$ content of gas at or near the airway of subject 12 to fluctuate and valid breaths.

The volume and/or flow rate of gas movement associated with anatomical events that cause the $CO_2$ content of gas at or near the airway of subject 12 to fluctuate are relatively small as in cardiogenic oscillations where the beating of the heart near the lung within the chest causes small non-productive gas movements of less than 20 ml/beat. Valid breathing typically involves gas movement with much larger volume s greater than the airway dead volume (e.g., ~150 ml in adults) and/or flow rate. As such, dilution of gas in the airway proximate to sampling interface 26 by the diluting flow of gas during anatomical events that cause the $CO_2$ content of gas at or near the airway of subject 12 to fluctuate has a much larger impact on the $CO_2$ content of gas drawn into gas inlet 28 than the dilution of gas in the airway of subject 12 during actual breaths. Specifically, dilution by the diluting flow of gas during anatomical events that cause the $CO_2$ content of gas at or near the airway of subject 12 to fluctuate will significantly reduce the amount of the fluctuation of $CO_2$ content in gas drawn into gas inlet 28 during such events.

However, because the volume and/or movement of gas in the airway of subject 12 during anatomical events that cause the $CO_2$ content of gas at or near the airway of subject 12 to fluctuate, the volume and/or flow rate of diluting flow of gas can be relatively small. In system 10, the diluting flow generator 19 is configured to generate diluting flow of gas such that the flow rate of the diluting flow of gas as the diluting flow of gas exits gas outlet 30 does not impact actual respiration by subject 12. This means that the diluting flow of gas does not elevate pressure within the airway of subject 12, impede gas flowing into or out of the airway of subject 12, and/or alter the composition of gas breathed into the lungs of subject 12 during respiration in a clinically significant manner. By way of non-limiting example, in one embodiment in which sampling interface 26 is configured to place gas outlet 30 in one or both of the nares of subject 12, the flow rate of the diluting flow of gas flowing into a nare of subject 12 is less than about 2 liters per minute. The sampling interface 26 may be configured such that the directionality of the diluting flow of gas as it is released by gas outlet 30 aids in keeping the diluting flow of gas from impacting respiration of subject 12.

In one embodiment, electronic storage 20 comprises electronic storage media that electronically stores information. The electronically storage media of electronic storage 20 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 20 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 20 may store software algorithms, information determined by processor 24, information received via user interface 22, output signals generated by composition detector 18, and/or other information that enables system 10 to function properly. Electronic storage 20 may be a separate component within system 10, or electronic storage 20 may be provided integrally with one or more other components of system 10 (e.g., processor 24).

User interface 22 is configured to provide an interface between system 10 and a user (e.g., subject 12, a caregiver, a researcher, etc.) through which the user may provide information to and receive information from system 10. This enables data, results, and/or instructions and any other communicable items, collectively referred to as "information," to be communicated between the user and system 10. Examples of interface devices suitable for inclusion in user interface 22 include a keypad, buttons, switches, a keyboard, knobs, levers, a display screen, a touch screen, speakers, a microphone, an indicator light, an audible alarm, and a printer. In one embodiment, user interface 22 actually includes a plurality of separate interfaces.

It is to be understood that other communication techniques, either hard-wired or wireless, are also contemplated by the present invention as user interface 22. For example, the present invention contemplates that user interface 22 may be integrated with a removable storage interface provided by memory 20. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 include, but are not limited to, an RS-232 port, RF link, an IR link, modem (telephone, cable or other). In short, any technique for communicating information with system 10 is contemplated by the present invention as user interface 22.

The one or more processors 24 are configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device, or processor 24 may represent processing functionality of a plurality of devices operating in coordination.

As is shown in FIG. 1, processor 24 may be configured to execute one or more computer program modules. The one or more computer program modules may include one or more of a breathing parameter module 42, a dilution generator control module 44, and/or other modules. Processor 24 may be configured to execute modules 42 and/or 44 by software; hardware; firmware; some combination of software, hardware, and/or firmware; and/or other mechanisms for configuring processing capabilities on processor 24.

It should be appreciated that although modules 42 and/or 44 are illustrated in FIG. 1 as being co-located within a single processing unit, in implementations in which processor 24 includes multiple processing units, one or more of modules 42 and/or 44 may be located remotely from the other modules. The description of the functionality provided by the different modules 42 and/or 44 described below is for illustrative purposes, and is not intended to be limiting, as any of modules 42 and/or 44 may provide more or less functionality than is described. For example, one or more of modules 42 and/or 44 may be eliminated, and some or all of its functionality may be provided by other ones of modules 42 and/or 44. As another example, processor 24 may be configured to execute one or more additional modules that may perform some or all of the functionality attributed below to one of modules 42 and/or 44.

The breathing parameter module 42 is configured to determine, from the output signals of composition detector 18, one or more parameters of the breathing of subject 12 that involve discriminating between anatomical events that cause the $CO_2$ content of gas at or near the airway of subject 12 to fluctuate and valid breaths. For example, such breathing parameters may include one or more of respiratory rate, breathing transitions, valid breath identification, and/or other parameters. As discussed above, because of the dilution of gas at or near the airway of subject 12 by diluting flow of gas, breathing parameter module 42 is able to distinguish between anatomical events that cause the $CO_2$ content of gas at or near the airway of subject 12 to fluctuate and valid breaths. Specifically, dilution by the diluting flow of gas tends to reduce $CO_2$ fluctuations caused by such events, thereby enabling fluctuation of $CO_2$ caused by valid breaths to stand out in the output signals of composition detector 18.

The dilution generator control module 44 is configured to control diluting flow generator 19 to selectively adjust one or more parameters of diluting flow of gas. For example, dilution generator control module 44 may control diluting flow generator 19 to adjust one or more of pressure, flow rate at gas outlet 30, and/or other parameters of the diluting flow of gas.

In one embodiment, dilution generator control module 44 controls diluting flow generator 19 to adjust the flow rate of diluting flow of gas over time such that the diluting flow of gas varies between breaths. This may include spiking the flow rate of the diluting flow of gas intermittently (e.g., from a predetermined lower level to a predetermined upper level), modulating the flow rate of the diluting flow of gas back and forth between predetermined high and low levels at a predetermined frequency, switching the flow rate of the diluting flow of gas to levels that are determined randomly (or pseudo-randomly), and/or otherwise varying the flow rate of the diluting flow of gas in a known manner.

A variation in the flow rate of the diluting flow of gas will cause a change in the amount of dilution effected by the diluting flow of gas at or near the airway of subject 12. If subject 12 is actually breathing, this change in dilution will have little to no appreciable effect on detected $CO_2$ levels (e.g., because the amount of $CO_2$ in a valid breath is much greater than the dilution gas at either flow rate). On the other hand, if subject 12 is not effectively breathing, but is instead experiencing anatomical events that cause the $CO_2$ content of gas at or near the airway of subject 12 to fluctuate, the change in dilution caused by switching the flow rate of the diluting flow of gas will have a significant impact on the detected $CO_2$ levels in two breaths during which the flow rate of the diluting flow of gas is different.

In one embodiment, as dilution generator control module 44 controls diluting flow generator 19 to adjust the flow rate of the diluting flow of gas in a known manner, breathing parameter module 42 uses the known adjustments in flow rate to further distinguish between valid breaths and anatomical events that cause the $CO_2$ content of gas at or near the airway of subject 12 to fluctuate. For example, if a change in the flow rate of the diluting flow of gas between two breaths results in little to no change in detected $CO_2$ content (as indicated by the output signals of composition detector 18), then breathing parameter module 42 determines that valid breathing is occurring. However, if a change in the flow rate of the diluting flow of gas results in a change in detected $CO_2$, then breathing parameter module 42 regards fluctuations in $CO_2$ as not being indicative of valid breaths.

It will be appreciated that although in FIG. 1 system 10 is shown as a side-stream capnometry system, this is not intended to be limiting. The principles described herein with respect to implementation of the diluting flow of gas to distinguish between anatomical events that cause the $CO_2$ content of gas at or near the airway of subject 12 to fluctuate and valid breaths from the output signals of composition detector 18 could be employed in a mainstream capnometry system without departing from the scope of this disclosure.

In a variety of therapeutic settings, a breathable substance is delivered to the airway of subject 12. In one embodiment, interface appliance 14 includes a therapeutic interface 46, as well as sampling interface 26. The therapeutic interface 46 is configured to deliver the breathable substance to the airway of subject 12. The breathable substance may include, for example, a flow of breathable gas. One or more parameters of the flow of breathable gas may be controlled according to a therapeutic regime to provide a therapeutic benefit to subject 12. The one or more parameters may include, for example, pressure, temperature, humidity, composition (e.g., oxygen enriched, etc.), flow rate, and/or other parameters. By way of non-limiting example, the therapy regime may provide positive airway support, non-invasive ventilation, oxygen supply, and/or other therapeutic benefits. The flow of breathable gas may be generated by a pressure generator, and/or some other device configured to generate a flow of breathable gas. In one embodiment, diluting flow generator 19 may obtain gas for the diluting flow of gas from the flow of breathable gas generated by the pressure generator. The breathable substance (e.g., the flow of breathable gas) may be provided to therapeutic interface 46 for delivery to the airway of subject 12 via a therapy conduit 48 coupled to therapeutic interface 26.

The sampling interface 26 is configured to engage a first set of one or more external orifices of the airway of subject 12, and therapeutic interface 46 is configured to engage a second set of one or more external orifices of the airway of subject 12. Through the first set of one or more external orifices, sampling interface 26 draws gas into gas inlet 28. Through the second set of one or more external orifices, therapeutic interface 46 delivers a breathable substance. In one embodiment, the second set of one or more external orifices of the airway of subject 12 include at least one external orifice of the airway of subject 12 that is not included in the first set of one or more external orifices.

For example, therapeutic interface 46 may include a mask (e.g., a nasal mask, a nasal/oral mask, a full face mask, a total face mask, a partial rebreathing mask, etc.) configured to enclose the second set of one or more external orifices of the airway of subject 12. In this example, the second set of one or more external orifices may include the mouth and/or the nares of subject 12. The sampling interface 26 may be provided by a cannula that is installed in the nares of subject 12, or in the mouth of subject 12, underneath the mask. The mask may enclose at least one external orifice of the airway of the subject not engaged by the cannula.

Figure 2:
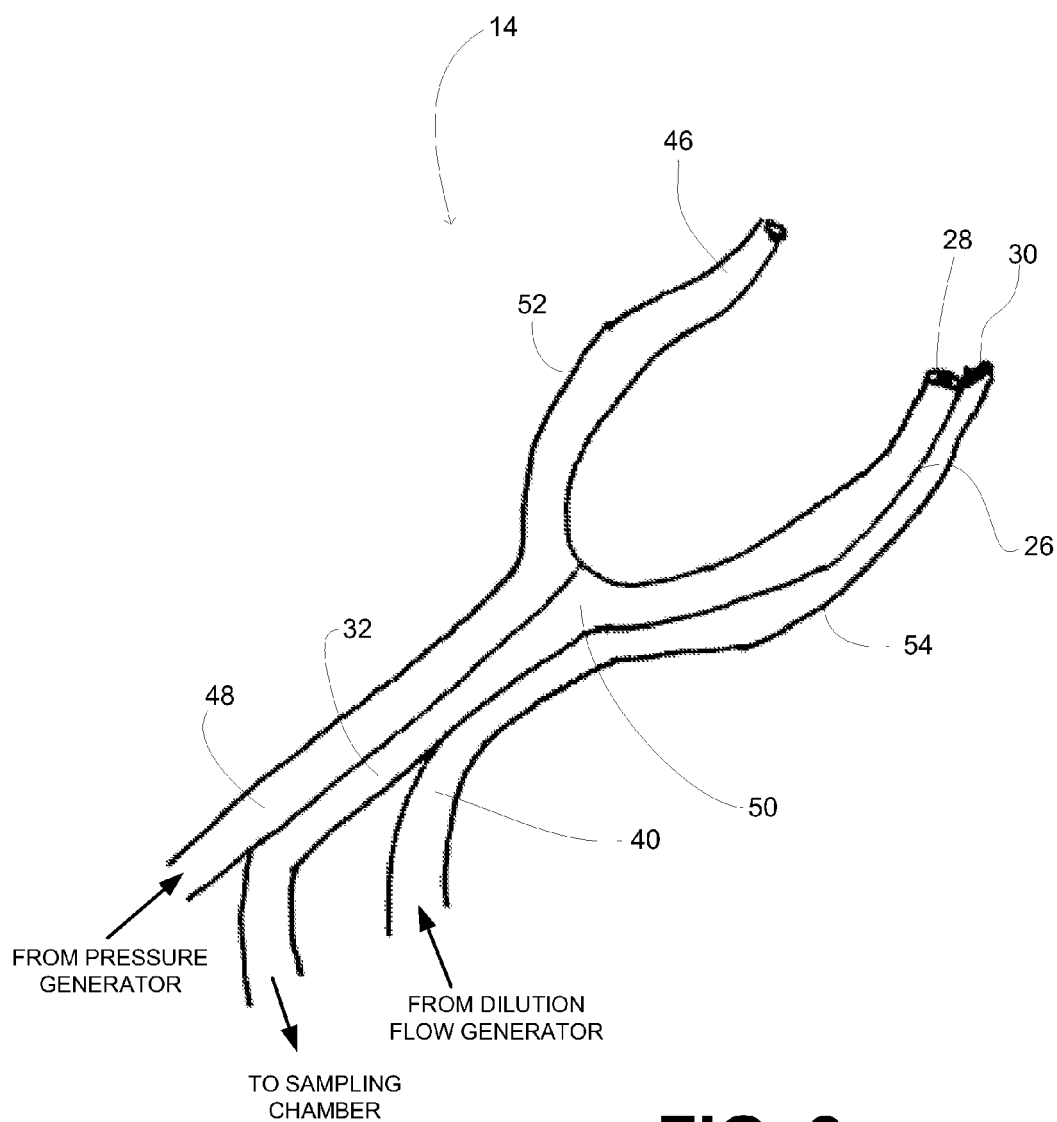
FIG. 2 illustrates a interface appliance, according to one or more embodiments of the invention.

In one embodiment, illustrated in FIG. 2, interface appliance 14 may include a single cannula 50. The cannula 50 may include a first hollow prong 52 and a second hollow prong 54 for engaging the nares of subject 12. In the embodiment shown, therapeutic interface 46 is formed by first hollow prong 52, which is used to deliver a therapeutic flow of breathable gas. The sampling interface 26 is formed by second hollow prong 54, which is used to draw gas into interface appliance 14 through gas inlet 28, and to deliver the diluting flow of gas through gas outlet 30 adjacent gas inlet 28. In this embodiment, sampling conduit 32, dilution conduit 40, and therapy conduit 48 may be formed as an integral, tri-lumen member.

Reference herein to interface appliance 14 do not necessarily imply that sampling interface 26 and therapeutic interface 46 are formed as a single, integral device. Sampling interface 26 and therapeutic interface 46 may be formed, and even installed on the face of subject 12 completely separately from each other. In one embodiment, interface appliance 14 includes only sampling interface 26. Other configurations for interface appliance 14 are included within the scope of this disclosure.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to monitor respiration of a subject, the system comprising:
    a subject interface appliance having a sampling interface including a gas inlet and a gas outlet, the subject interface appliance being configured to be installed at or near the airway of the subject such that gas from the airway of the subject is drawn into the gas inlet, the gas outlet being arranged near the gas inlet;
    a sampling chamber in fluid communication with the subject interface appliance such that gas drawn from the airway of the subject that is drawn into the gas inlet flows into the sampling chamber;
    a sensor configured to generate an output signal conveying information related to the carbon dioxide content of gas in the sampling chamber;
    a processor configured to determine, from the output signal generated by the sensor, one or more parameters of the respiration of the subject and to distinguish between breaths and other anatomical events that cause fluctuations in carbon dioxide content in the airway of the subject based solely on the output signal of the sensor; and
    a diluting flow generator configured to generate a diluting flow of gas, the diluting flow generator being in fluid communication with the subject interface appliance such that the diluting flow of gas is emitted from the gas outlet at or near the gas inlet, wherein:
    the diluting flow of gas is substantially free of carbon dioxide, and is emitted by the gas outlet with a flow rate and directionality (i) that dilutes gas from the airway of the subject prior to the gas being drawn into the gas inlet of the subject interface appliance such that the processor is able to distinguish between (i)(a) the breaths and (i)(b) the other anatomical events that cause fluctuations in the carbon dioxide content in the airway of the subject based solely on the output signal of the sensor, and (ii) that does not impact the respiration of the subject, and
    the diluting flow of gas is further configured (iii) such that (iii)(a) during anatomical events that cause the carbon dioxide content of gas at or near the airway of the subject to fluctuate, the diluting flow of gas has a much larger impact on the carbon dioxide of gas drawn into the gas inlet than (iii)(b) during actual breaths.

2. The system of claim 1, wherein the one or more parameters of the respiration of the subject include one or more of a respiration rate of the subject, a timing of a breathing transition of the subject, or an identification of a valid breath.

3. The system of claim 1, wherein the subject interface appliance further comprises a therapy interface configured to deliver a therapeutic flow of breathable gas to the airway of the subject that has a therapeutic benefit to the respiration of the subject, wherein the therapy interface is separate from the sampling interface such that the therapeutic flow of breathable gas is a separate and distinct flow of gas from the diluting flow of gas.

4. The system of claim 3, wherein the sampling interface is configured such that the gas outlet emits the diluting flow of gas into a first set of one or more external orifices of the airway of the subject, wherein the therapy interface is configured to deliver the therapeutic flow of breathable gas to a second set of one or more external orifices of the airway of the subject, and wherein the second set of one or more external orifices of the airway of the subject includes at least one external orifice of the airway of the subject that is not included in the first set of one or more external orifices of the airway of the subject.

5. The system of claim 1, wherein the diluting flow generator is configured to generate the diluting flow of gas such that the flow rate of the diluting flow of gas as it is emitted from the gas outlet of the sampling interface varies in a known manner, and wherein determination of the one or more parameters of the breathing of the subject by the processor is based on the known flow rate of the diluting flow of gas as the flow rate of the diluting flow of gas varies.

6. A method of monitoring respiration of a subject, the method comprising:
    drawing gas, via a subject interface appliance, through a gas inlet positioned at or near the airway of a subject and into a sampling chamber;
    generating, via a composition detector, an output signal conveying information related to the carbon dioxide content of gas in the sampling chamber;
    determining, via a processor, from the output signal generated, one or more parameters of the respiration of the subject;
    generating, via a diluting flow generator, a diluting flow of gas that is substantially free of carbon dioxide;
    emitting, via an outlet, the diluting flow of gas at a location and flow rate (i) that dilutes gas from the airway of the subject prior to the gas being drawn into the gas inlet of the subject interface appliance such that the processor is able to distinguish between (i)(a) breaths and (i)(b) other anatomical events that cause fluctuations in carbon dioxide content in the airway of the subject based solely on the output signal, and (ii) that does not impact respiration of the subject, and wherein the diluting flow of gas is further emitted (iii) such that (iii)(a) during anatomical events that cause the carbon dioxide content of gas at or near the airway of the subject to fluctuate, the diluting flow of gas has a much larger impact on the carbon dioxide of gas drawn into the gas inlet than (iii)(b) during actual breaths; and
    distinguishing between the breaths and the other anatomical events that cause fluctuations in the carbon dioxide content in the airway of the subject based solely on the output signal of the sensor.

7. The method of claim 6, wherein the one or more parameters of the respiration of the subject include one or more of a respiration rate of the subject, a timing of a breathing transition of the subject, or an identification of a valid breath.

8. The method of claim 6, further comprising delivering a therapeutic flow of breathable gas to the airway of the subject that has a therapeutic benefit to the respiration of the subject such that the therapeutic flow of breathable gas is a separate and distinct flow of gas from the diluting flow of gas.

9. The method of claim 8, wherein drawing gas through the gas inlet comprises drawing gas from a first set of one or more external orifices of the airway of the subject, wherein delivering the therapeutic flow of flow of breathable gas comprises delivering the therapeutic flow of breathable gas to a second set of one or more external orifices of the airway of the subject, and wherein the second set of one or more external orifices of the airway of the subject includes at least one external orifice of the airway of the subject that is not included in the first set of one or more external orifices of the airway of the subject.

10. The method of claim 6, further comprising varying the flow rate of the diluting flow of gas as it is emitted from the gas outlet in a known manner, and wherein determining the one or more parameters of the breathing of the subject by the processor is based on the known flow rate of the diluting flow of gas as the flow rate of the diluting flow of gas varies.

11. A system configured to monitor respiration of a subject, the system comprising:
means for drawing gas through a gas inlet positioned at or near the airway of a subject and into a sampling chamber, wherein the means for drawing gas comprises a subject interface appliance;
means for generating an output signal conveying information related to the carbon dioxide content of gas in the sampling chamber, wherein the means for generating the output signal comprises a sensor;
means for determining, from the output signal generated, one or more parameters of the respiration of the subject and for distinguishing between breaths and other anatomical events that cause fluctuations in carbon dioxide content in the airway of the subject based solely on the output signal of the sensor, wherein the means for determining comprises a processor;
means for generating a diluting flow of gas that is substantially free of carbon dioxide; and
means for emitting the diluting flow of gas at a location and flow rate (i) that dilutes gas from the airway of the subject prior to the gas being drawn into the gas inlet of the subject interface appliance such that the processor is able to distinguish between (i)(a) the breaths and (i)(b) the other anatomical events that cause fluctuations in the carbon dioxide content in the airway of the subject based solely on the output signal of the sensor, and (ii) that does not impact respiration of the subject, and wherein the diluting flow of gas is further emitted (iii) such that (iii)(a) during anatomical events that cause the carbon dioxide content of gas at or near the airway of the subject to fluctuate, the diluting flow of gas has a much larger impact on the carbon dioxide of gas drawn into the gas inlet than (iii)(b) during actual breaths.

12. The system of claim 11, wherein the one or more parameters of the respiration of the subject include one or more of a respiration rate of the subject, a timing of a breathing transition of the subject, or an identification of a valid breath.

13. The system of claim 11, further comprising means for delivering a therapeutic flow of breathable gas to the airway of the subject that has a therapeutic benefit to the respiration of the subject such that the therapeutic flow of breathable gas is a separate and distinct flow of gas from the diluting flow of gas.

14. The system of claim 13, wherein the means for drawing gas through the gas inlet is configured to draw gas from a first set of one or more external orifices of the airway of the subject, wherein the means for delivering the therapeutic flow of flow of breathable gas is configured to deliver the therapeutic flow of breathable gas to a second set of one or more external orifices of the airway of the subject, and wherein the second set of one or more external orifices of the airway of the subject includes at least one external orifice of the airway of the subject that is not included in the first set of one or more external orifices of the airway of the subject.

15. The system of claim 11, further comprising varying the flow rate of the diluting flow of gas as it is emitted from the gas outlet in a known manner, and wherein determining the one or more parameters of the breathing of the subject by the processor is based on the known flow rate of the diluting flow of gas as the flow rate of the diluting flow of gas varies.

16. A system configured to monitor respiration of a subject, the system comprising:
a subject interface appliance that draws gas through a gas inlet positioned at or near the airway of a subject and into a sampling chamber;
a sensor that generates an output signal conveying information related to the carbon dioxide content of gas in the sampling chamber;
a processor that determines, from the output signal generated, one or more parameters of the respiration of the subject and distinguishes between breaths and other anatomical events that cause fluctuations in carbon dioxide content in the airway of the subject based solely on the output signal of the sensor; and
a diluting flow generator that dilutes a flow of gas that is substantially free of carbon dioxide, wherein:
the flow of gas is diluted at a location and flow rate (i) that dilutes gas from the airway of the subject prior to the gas being drawn into the gas inlet of the subject interface appliance such that the processor is able to distinguish between (i)(a) the breaths and (i)(b) the other anatomical events that cause fluctuations in the carbon dioxide content in the airway of the subject based solely on the output signal of the sensor, and (ii) that does not impact respiration of the subject, and
the diluting flow of gas is further configured (iii) such that (iii)(a) during anatomical events that cause the carbon dioxide content of gas at or near the airway of the subject to fluctuate, the diluting flow of gas has a much larger impact on the carbon dioxide of gas drawn into the gas inlet than (iii)(b) during actual breaths.

17. The system of claim 16, wherein the one or more parameters of the respiration of the subject include one or more of a respiration rate of the subject, a timing of a breathing transition of the subject, or an identification of a valid breath.

18. The system of claim 16, wherein the subject interface appliance further comprises a therapy interface that delivers a therapeutic flow of breathable gas to the airway of the subject that has a therapeutic benefit to the respiration of the subject such that the therapeutic flow of breathable gas is a separate and distinct flow of gas from the diluting flow of gas.

19. The system of claim 18, wherein:
the subject interface appliance is configured to draw gas from a first set of one or more external orifices of the airway of the subject,
the therapy interface is configured to deliver the therapeutic flow of breathable gas to a second set of one or more external orifices of the airway of the subject, and
the second set of one or more external orifices of the airway of the subject includes at least one external orifice of the airway of the subject that is not included in the first set of one or more external orifices of the airway of the subject.

20. The system of claim 16, further comprising varying the flow rate of the diluting flow of gas as it is emitted from the gas outlet in a known manner, and wherein determining the one or more parameters of the breathing of the subject by the processor is based on the known flow rate of the diluting flow of gas as the flow rate of the diluting flow of gas varies.

21. The system of claim 1, wherein the diluting flow generator generates the diluting flow of gas such that the amount of the diluting flow of gas at the subject's airway, for all flow rates of the diluting flow of gas generated by the diluting flow generator, is less than the amount of carbon dioxide content within a breath of the subject.

* * * * *